United States Patent [19]

Fujiwara et al.

[11] Patent Number: 4,490,524
[45] Date of Patent: Dec. 25, 1984

[54] 23-O-ACYL-23-DEMYCINOSYLDE-SMYCOSIN DERIVATIVES

[75] Inventors: Tatsuro Fujiwara; Hideyuki Watanabe; Takao Hirano; Hideo Sakakibara, all of Shizuoka, Japan

[73] Assignee: Toyo Jozo Kabushiki Kaisha, Shizuoka, Japan

[21] Appl. No.: 460,443

[22] Filed: Jan. 24, 1983

[30] Foreign Application Priority Data

Jan. 22, 1982 [JP] Japan ................................ 57-9396
Apr. 28, 1982 [JP] Japan ................................ 57-71803
May 10, 1982 [JP] Japan ................................ 57-78895

[51] Int. Cl.$^3$ ............................................. C07H 17/08
[52] U.S. Cl. ........................................ 536/7.1; 536/115
[58] Field of Search .................................. 536/7.1, 115

[56] References Cited

U.S. PATENT DOCUMENTS 4,141,971  2/1979  Krausz et al. ........................ 536/7.1

FOREIGN PATENT DOCUMENTS 0005000  1/1982  Japan ................................... 536/7.1
2081711  2/1982  United Kingdom .................. 536/7.1

OTHER PUBLICATIONS

Tetrahedron Letters, No. 54, pp. 4737–4740, 1970, "The Structure of Tylosin[1,2]", by R. B. Morin et al.
The Journal of Antibiotics, vol. XXXIV, No. 10, pp. 1374–1376, "Synthesis of 4'-Deoxymycaminosyl Tylonolide".

Primary Examiner—Johnnie R. Brown
Assistant Examiner—Elli Peselev
Attorney, Agent, or Firm—Young & Thompson

[57] ABSTRACT

Compounds of the formula

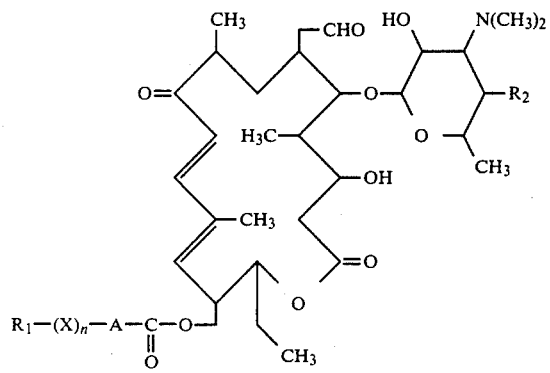

wherein $R_1$ is optionally substituted phenyl, thienyl, 2-amino-4-thiazolyl or 2-chloroacetamido-4-thiazolyl; A is lower alkylene, lower alkenylene, or lower alkylene substituted by lower alkyl, amino, lower alkoxyimino or phenyl-Z-group wherein Z is a single bond or —S— or —SO$_2$—, but when $R_1$ is 2-amino-4-thiazolyl or 2-chloroacetamido-4-thiazolyl then A is lower alkylene substituted by lower alkoxyimino; $R_2$ is hydrogen or hydroxyl; X is oxygen or sulfur and n=0 or 1, or a non-toxic salt thereof. These compounds have a stronger antibacterial activity against Gram positive bacteria as compared with known macrolide antibiotics such as erythromycin and tylosin, and also have an equivalent level of antibacterial activity against Gram negative bacteria as compared with that of erythromycin, and hence may be useful for clinical use. These compounds are also useful for feed additives and growth stimulants.

2 Claims, No Drawings

23-O-ACYL-23-DEMYCINOSYLDESMYCOSIN DERIVATIVES

This invention relates to novel .23-O-acyl-23-demycinosyldesmycosin derivatives. More particularly the present invention pertains to compounds of the formula

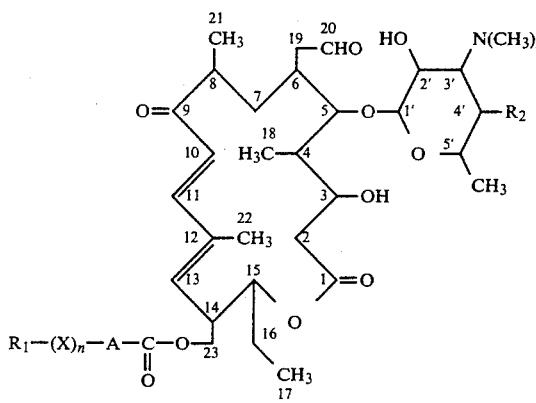

wherein $R_1$ is optionally substituted phenyl, thienyl, 2-amino-4-thiazolyl or 2-chloroacetamido-4-thiazolyl; A is lower alkylene, lower alkenylene, or lower alkylene substituted by lower alkyl, amino, lower alkoxyimino or phenyl-Z-group wherein Z is a single bond or —S— or —SO$_2$—, but when $R_1$ is 2-amino-4-thiazolyl or 2-chloroacetamido-4-thiazolyl then A is lower alkylene substituted by lower alkoxyimino; $R_2$ is hydrogen or hydroxyl; X is oxygen or sulfur and n=0 or 1, or a non-toxic salt thereof.

Examples of pharmaceutically acceptable salts are salts of inorganic acids such as hydrochlorides, sulfates or phosphates and salts of organic acids such as acetates, propionates, tartrates, citrates, succinates, malates, aspartates or glutamates. Other non-toxic salts can be used.

The novel compound [1] has a stronger antibacterial activity against Gram positive bacteria as compared with known macrolide antibiotics such as erythromycin and tylosin, and also has an equivalent level of antibacterial activity against Gram negative bacteria as compared with that of erythromycin, and hence may be useful for clincal use. The antibiotic also is useful for feed additives and growth stimulants.

A compound [1] of the present invention is produced by the following processes:

A starting material of the formula

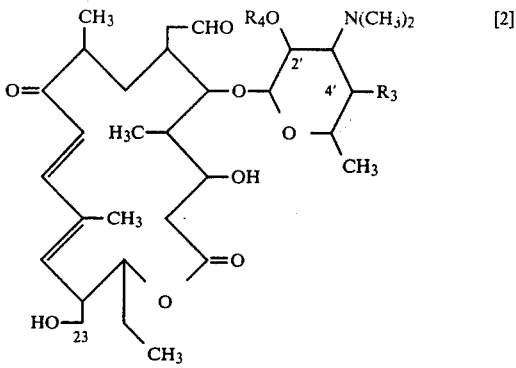

wherein $R_3$ is hydrogen or —OR$_4$ in which R$_4$ is a protective group for hydroxyl, is acylated at the hydroxyl at position-23 with a carboxylic acid of the formula

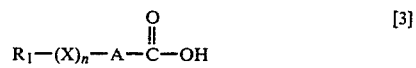

wherein $R_1$, X, A and n have the same meanings hereinabove, or a reactive derivative thereof, and the protective group for hydroxyl at positions-2' and -4', or position-2' is removed.

The starting material [2] of the present invention wherein $R_3$ is OR$_4$, in which R$_4$ is a protective group for hydroxyl, is a compound in which the hydroxyl at positions-2' and -4' of 23-demycinosyldesmycosin [Tetrahedron Letters, 4737 (1970)] is protected, and a compound [2] wherein $R_3$ is hydrogen, is a compound in which the hydroxyl at position-2' of 23-demycinosyl-4'-deoxydesmycosin [J. Antibioti., 34 (10), 1374–1376 (1981), Jap. Pat. Unexam. Publ. No. 57-28100] is protected.

Examples of protective groups are lower alkanoyls such as acetyl, propionyl or butyryl and halogenated acetyls such as chloroacetyl, dichloroacetyl, trichloroacetyl or trifluoroacetyl. Acetyl is preferred.

Introduction of the acetyl can be effected by reacting 23-demycinosyldesmycosin or 23-demycinosyl-4'-deoxydesmycosin with acetic anhydride in an inert organic solvent. Preferred examples of inert organic solvents are dichloromethane, chloroform, dichloroethane or acetone. The reaction proceeds at room temperature, and can be checked by silica gel thin layer chromatography (TLC) or high performance liquid chromatography (HPLC), and can be stopped upon observing the disappearance of 23-demycinosyldesmycosin or 23-demycinosyl-4'-deoxydesmycosin.

The reaction product [2] can be isolated from the reaction mixture by adding water to the reaction mixture and extracting with a water-immiscible organic solvent such as chloroform, dichloroethane, methyl isobutyl ketone, ethyl acetate or butyl acetate at an alkaline pH 8–9.5. Further purification can be effected by column chromatography using silica gel, active alumina or an adsorption resin with an appropriate solvent such as benzene-acetone or chloroform-methanol.

Acylation of the hydroxyl at position-23 in the starting substance [2] can be performed by reacting substance [2] with carboxylic acid [3] or its reactive derivative.

The above carboxylic acid [3] is a carboxylic acid having a ring side chain and at least one carbon chain between ring and carboxyl, and the ring is phenyl, thienyl or thiazolyl. These groups may optionally be substituted by preferred substitutents. For example, phenyl can be substituted by 1 or 2 lower alkyls, lower alkoxys or halogens, and thiazolyl can be substituted by amino or substituted amino. The above carbon chain is lower alkylene or lower alkenylene, and may optionally be bound to the ring through oxygen or sulfur. The said lower alkylene is optionally substituted by lower alkyl, amino, lower alkoxyimino, phenyl, phenylthio or phenylsulfonyl. The phenyl may optionally have substituent groups.

Examples of the above carboxylic acids are phenyl lower fatty acids such as phenylacetic acid, α-phenylpropionic acid, β-phenylpropionic acid, α-phenylbutyric acid or α-phenylisobutyric acid; phenyl-lower unsaturated fatty acids such as cinnamic acid; phenoxy-lower fatty acids such as phenoxyacetic acid or α-(p-chlorophenoxy)-isobutyric acid; phenylthio-lower fatty acids such as phenylthioacetic acid; α-amino-phenyl lower fatty acids such as D-(−)-phenylglycine or D-(−)-p-hydroxy-phenylglycine; 2-phenyl-2-lower alkoxyiminoacetic acids such as 2-phenyl-2-methoxyiminoacetic acid; thienyl-lower fatty acids such as 2-thienylacetic acid; thiazoleacetic acids such as 2-(2-aminothiazole-4-yl)-2-methoxyiminoacetic acid, 2-(2-chloroacetamide-thiazole-4-yl)-2-methoxyiminoacetic acid; diphenyl-lower fatty acids such as diphenylacetic acid; α-phenylthiophenyl-lower fatty acids such as α-phenylthio-phenylacetic acid; and α-phenylsulfonyl-phenyl-lower fatty acids such as α-phenylsulfonyl-phenylacetic acid. The functional groups in these carboxylic acids such as amino or hydroxyl are preferably first protected.

Examples of the above reactive derivatives are acid halides, acid anhydrides, mixed anhydrides or activated esters such as p-nitrophenyl ester, p-nitrophenylthio ester, cyanomethyl ester, N-hydroxysuccinimide ester of N-hydroxyphthalimide ester. Commonly known other acylating reagents can be used. Direct condensation of the carboxylic acid can also be performed by use of a condensation reagent, for example, carbodiimides such as N,N'-dicyclohexyl carbodiimide (DCC), N,N'-bis(p-dimethylaminophenyl)carbodiimide, N-cyclohexyl-N'-2(morpholyl-4-ethyl)carbodiimide, or N-ethyl-N'-dimethylaminopropyl-carbodiimide; N,N'-carbonyldiimidazoles such as 1,1'-carbonyldiimidazole or 1,1'-thisocarbonyldiimidazole and azodicarboxylic acid diethyl ester/triphenyl phosphine.

The acylation reaction can be conducted in a non-protonic solvent. Examples of non-protonic solvents are dichloromethane, chloroform, dichloroethane, tetrahydrofuran, dioxane or benzene. The reaction proceeds at room temperature and it is not necessary to cool or heat unless the rate of reaction is too slow or fast. The reaction can be traced by silica gel TLC, and is terminated upon observing the disappearance of the starting material [2]. In the above acylating reaction, if acid is formed, a tertiary organic base such as triethylamine, pyridine, picoline, collidine, quinoline, N-methylmorpholine, tribenzylamine, or dimethylamine is preferably first added. Isolation of the compound, obtained by the above acylation, of the formula

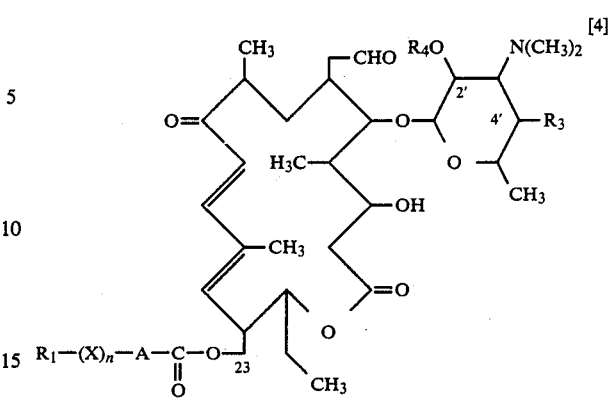

wherein $R_1$, $R_3$, $R_4$, X, A and n have the same meanings hereinabove, can be effected by adding water to the reaction mixture and extracting with a water-immiscible organic solvent such as chloroform, dichloroethane, methyl isobutyl ketone, ethyl acetate or butyl acetate, at an alkaline pH 8–9.5. Further purification can be effected by column chromatography.

Removal of the protective group for the hydroxyl at positions-2' and -4', or position-2' of the product [4], especially acetyl, is effected under heating in a lower alcohol optionally containing water. Examples of lower alcohols are methanol or ethanol. The reaction can be tracted by silica gel TLC and is terminated upon the disappearance of the product [4].

Any protective gropus in the product [4] can be removed by known methods. Isolation of the product [1] from the reaction mixture can be performed by distilling off the lower alkanol, and extracting with a water-immiscible organic solvent such as chloroform, dichloroethane, methyl isobutyl ketone, ethyl acetate or butyl acetate, at an alkaline pH 8–9.5. Further purification can be performed by chromatography using silica gel, active alumina or an adsorption agent.

The minimum inhibitory concentration (MIC) (mcg/ml) of the product [1] of the present invention is shown in the following table. The numbers in the table have the following meanings:

| $R_1-(X)_n-A-CO-$ | $R_2$ |
|---|---|
| 1. ⌬—CH₂CO— | OH |
| 2. ⌬—S—CH₂CO— | OH |
| 3. ⌬—CH=CHCO— | OH |
| 4. ⌬—CHCO—<br>     \|<br>     C₂H₅ | OH |

| | R₁—(X)ₙ—A—CO— | R₂ |
|---|---|---|
| 5. | D(−)— phenyl-CH(NH₂)—CO— | OH |
| 6. | thiophene-2-yl-CH₂CO— | OH |
| 7. | ClCH₂CONH—(thiazol-2-yl)—C(=N—OCH₃)—CO— | OH |
| 8. | 4-Cl-C₆H₄—O—C(CH₃)₂—CO— | OH |
| 9. | (C₆H₅)₂CH—CO— | OH |
| 10. | phenyl-CH(S-phenyl)—CO— | OH |
| 11. | phenyl-CH(SO₂-phenyl)—CO— | OH |
| 12. | C₆H₅—CH₂CO— | H |
| 13. | C₆H₅—S—CH₂CO— | H |
| 14. | C₆H₅—CH=CHCO— | H |
| 15. | C₆H₅—CH(C₂H₅)—CO— | H |
| 16. | thiophene-2-yl-CH₂CO— | H |

EM: erythromycin, TS: tylosin.
*macrolide resistant A group bacteria (clinical isolates of erythromycin, oleandomycin and 16-membered macrolide antibiotic resistant strains.)

| | sample | | | | | | | | |
|---|---|---|---|---|---|---|---|---|---|
| Test organisms | 1 | 2 | 3 | 4 | 5 | 6 | 7 | EM | TS |
| *Staph. aureus* ATCC 6538p | ≦0.05 | ≦0.05 | 0.1 | ≦0.05 | 0.1 | ≦0.05 | 0.1 | 0.1 | 0.8 |
| *Staph. aureus* MS353 | ≦0.05 | ≦0.05 | 0.2 | ≦0.05 | 0.2 | ≦0.05 | 0.2 | 0.1 | 0.8 |
| *Staph. aureus* MS353 AO* | >100 | >100 | 50 | 25 | >100 | >100 | 12.5 | >100 | >100 |
| *Staph. aureus* 012.7* | >100 | >100 | 50 | 100 | >100 | >100 | 25 | >100 | >100 |
| *Staph. epidermidis* ap-al-l | ≦0.05 | ≦0.05 | ≦0.05 | ≦0.05 | 0.1 | ≦0.05 | 0.2 | 0.1 | 0.4 |
| *Strept. pyogenes* N.Y. 5 | ≦0.05 | ≦0.05 | ≦0.05 | ≦0.05 | ≦0.05 | ≦0.05 | ≦0.05 | ≦0.05 | 0.1 |
| *Strept. pyogenes* 1022* | >100 | >100 | 25 | 50 | >100 | >100 | 50 | 50 | 25 |
| *Strept. faecalis* 1501 | ≦0.05 | ≦0.05 | 0.4 | 0.1 | 0.2 | ≦0.05 | 0.4 | 0.2 | 1.6 |
| *Strept. agalactiae* 1020 | ≦0.05 | ≦0.05 | ≦0.05 | ≦0.05 | 0.1 | ≦0.05 | ≦0.05 | ≦0.05 | 0.4 |
| *Sarcina lutea* ATCC 9341 | ≦0.05 | ≦0.05 | ≦0.05 | ≦0.05 | ≦0.05 | ≦0.05 | ≦0.05 | ≦0.05 | ≦0.05 |
| *Corynebact. diphtheriae* P.W.8 | ≦0.05 | ≦0.05 | ≦0.05 | ≦0.05 | ≦0.05 | ≦0.05 | ≦0.05 | ≦0.05 | ≦0.05 |
| *Bacillus subtilis* ATCC 6633 | ≦0.05 | ≦0.05 | 0.1 | ≦0.05 | 0.2 | ≦0.05 | ≦0.05 | ≦0.05 | 0.2 |
| *E. coli* NIHJ-JC2 | 25 | 25 | >100 | 50 | 100 | 50 | >100 | 50 | >100 |
| *Salm. typhosa* H 901 | 50 | 50 | >100 | 100 | 100 | 50 | >100 | 50 | >100 |
| *Kleb. pneu moniae* ATCC 10031 | 1.6 | 1.6 | 3.1 | 3.1 | 3.1 | 6.3 | 12.5 | 6.3 | 100 |
| *Shigella sonnei* E 33 | 25 | 25 | >100 | 25 | 50 | 50 | >100 | 50 | >100 |
| *Proteus vul garis* OX 19 | 3.1 | 3.1 | 25 | 6.3 | 12.5 | 25 | 25 | 25 | >100 |
| *Pseud. aeruginosa* IAM 1095 | 12.5 | 12.5 | >100 | 12.5 | 50 | 100 | 50 | 100 | >100 |

| | Sample | | | | | |
|---|---|---|---|---|---|---|
| Test organisms | 8 | 9 | 10 | 11 | EM | TS |
| *Staphylococcus aureus* ATCC 6538p | ≦0.05 | 0.1 | 0.1 | 0.1 | 0.1 | 0.8 |
| *Staphylococcus aureus* MS 353 | 0.1 | 0.1 | 0.2 | 0.2 | 0.1 | 0.8 |
| *Staphylococcus aureus* MS 353AO* | 25 | 25 | 25 | >100 | >100 | >100 |

-continued

| | 50 | 25 | 50 | >100 | >100 | >100 |
|---|---|---|---|---|---|---|
| *Staphylococcus aureus* 0127* | 50 | 25 | 50 | >100 | >100 | >100 |
| *Staphylococcus epidermidis* ap-al-1 | ≦0.05 | ≦0.05 | 0.1 | ≦0.05 | 0.1 | 0.4 |
| *Streptococcus pyogenes* N.Y. 5 | ≦0.05 | ≦0.05 | ≦0.05 | ≦0.05 | ≦0.05 | 0.1 |
| *Streptococcus pyogenes* 1022* | 2.5 | 6.3 | 2.5 | 100 | >100 | >100 |
| *Streptococcus faecalis* 1501 | 0.1 | 0.1 | 0.4 | 0.1 | 0.2 | 1.6 |
| *Streptococcus agalactiae* 1020 | ≦0.05 | ≦0.05 | 0.1 | ≦0.05 | ≦0.05 | 0.4 |
| *Sarcina luten* ATCC 9341 | ≦0.05 | ≦0.05 | ≦0.05 | ≦0.05 | ≦0.05 | ≦0.05 |
| *Corynebacterium diphtheriae* P.W. 8 | ≦0.05 | ≦0.05 | ≦0.05 | ≦0.05 | ≦0.05 | ≦0.05 |
| *Bacillus subtilis* ATCC 6633 | 0.1 | 0.1 | 0.1 | 0.1 | ≦0.05 | 0.2 |
| *Escherichia coli* NIHJ-JC2 | 50 | >100 | 50 | >100 | 50 | >100 |
| *Salmonella typhosa* H 901 | >100 | >100 | >100 | >100 | 50 | >100 |
| *Klebsiella pneumoniae* ATCC 10031 | 3.1 | 25 | 25 | 25 | 6.3 | 100 |
| *Shigella sonnei* E 33 | 50 | >100 | 50 | 100 | 50 | >100 |
| *Proteus vulgaris* OX 19 | 12.5 | 6.3 | 12.5 | 25 | 25 | >100 |
| *Pseudomonas aeruginosa* IAM 1095 | 50 | >100 | >100 | 100 | 100 | >100 |

| Test organisms | Sample | | | | | | |
|---|---|---|---|---|---|---|---|
| | 12 | 13 | 14 | 15 | 16 | EM | TS |
| *Staphylococcus aureus* ATCC 6538 P | ≦0.05 | ≦0.05 | 0.1 | ≦0.05 | ≦0.05 | 0.1 | 0.8 |
| *Staphylococcus aureus* MS 353 | 0.1 | ≦0.05 | 0.2 | ≦0.05 | ≦0.05 | 0.1 | 0.8 |
| *Staphylococcus aureus* MS 353AO* | >100 | 100 | 25 | 50 | >100 | >100 | >100 |
| *Staphylococcus aureus* 0127 | >100 | >100 | 25 | 100 | >100 | >100 | >100 |
| *Staphylococcus epidermidis* ap-al-1 | ≦0.05 | ≦0.05 | ≦0.05 | ≦0.05 | ≦0.05 | 0.1 | 0.4 |
| *Streptococcus pyogenes* N.Y. 5 | ≦0.05 | ≦0.05 | ≦0.05 | ≦0.05 | ≦0.05 | ≦0.05 | 0.1 |
| *Streptococcus pyogenes* 1022* | >100 | >100 | 100 | 50 | >100 | >100 | >100 |
| *Streptococcus faecalis* 1501 | ≦0.05 | ≦0.05 | 0.2 | ≦0.05 | ≦0.05 | 0.2 | 1.6 |
| *Streptococcus agalactiae* 1020 | ≦0.05 | ≦0.05 | 0.1 | ≦0.05 | ≦0.05 | ≦0.05 | 0.4 |
| *Sarcina lutea* ATCC 9341 | ≦0.05 | ≦0.05 | ≦0.05 | ≦0.05 | ≦0.05 | ≦0.05 | ≦0.05 |
| *Corynebacterium diphtheriae* P.W. 8 | ≦0.05 | ≦0.05 | ≦0.05 | ≦0.05 | ≦0.05 | ≦0.05 | ≦0.05 |
| *Bacillus subtilis* ATCC 6633 | ≦0.05 | ≦0.05 | 0.1 | ≦0.05 | ≦0.05 | ≦0.05 | 0.2 |
| *Esherichia coli* NIHJ-JC 2 | 25 | 12.5 | >100 | 25 | 12.5 | 50 | >100 |
| *Samonella typhosa* H 901 | 25 | 25 | >100 | 50 | 25 | 50 | >100 |
| *Klebsiella pneumoniae* ATCC 10031 | 6.3 | 1.6 | 100 | 1.6 | 0.8 | 6.3 | 100 |
| *Shigella sonnei* E 33 | 12.5 | 12.5 | >100 | 25 | 12.5 | 50 | >100 |
| *Proteus vulgaris* OX 19 | 6.3 | 6.3 | 12.5 | 6.3 | 3.1 | 25 | >100 |
| *Pseudomonas aeruginosa* IAM 1095 | 100 | 50 | >100 | 50 | 50 | 100 | >100 |

The following examples illustrate the present invention. The Rf values in the examples are measured by TLC using the following carrier and developer, if not specified:

Carrier: Merck, DC-Fertigplatten Kieselgel 60 F 254, Art 5715.

Developer:
 a: benzene-acetone (3:1)
 b: chloroform-methanol (5:1)
 c: chloroform-methanol-conc. aq. ammonia (150:10:1)
 d: chloroform-methanol-conc. aq. ammonia (100:10:1)

EXAMPLE 1

2′,4′-di-O-acetyl-23-demycinosyldesmycosin:

Acetic anhydride (16.73 ml, 5 molar excess) was added to 23-demycinosyldesmycosin (21.21 g, 35.5 mM) dissolved in dichloromethane (105 ml) and the mixture was stirred at room temperature for 1.5 hours. The reaction mixture was poured into dil. aq. ammonia (400 ml) and extracted twice with chloroform (300 ml). The combined chloroform layer was dehydrated with anhydrous magnesium sulfate, and concentrated in vacuo to obtain 2′,4′-di-O-acetyl-23-demycinosyldesmycosin (24.01 g, yield: 99.3%).

TLC: $Rf_a = 0.32$ (23-demycinosyldesmycosin $Rf = 0.13$)

EXAMPLE 2

23-O-(2-thienylacetyl)-23-demycinosyldesmycosin:

N,N′-dicyclohexyl carbodiimide (DCC, 84.7 mg, 1.4 molar excess) dissolved in dichloromethane (1 ml) was added to 2′,4′-di-O-acetyl-23-demycinosyldesmycosin (200 mg, 0.2934 mM) and 2-thienylacetic acid (62.5 mg, 1.5 molar excess) dissolved in dichloromethane (1 ml) under cooling at 0° C., and the mixture was stirred at room temperature for 15 hours. Insoluble materials were removed by filtration, and the filtrate was added to dil. aq. ammonia (5 ml) and extracted three times with chloroform (20 ml). The chloroform layers were combined and dehydrated with anhydrous magnesium sulfate and concentrated in vacuo. The residue was purified by silica gel preparative TLC (developer: benzene-acetone, 3:1). The fractions showing $Rf_a = 0.55$ were collected and extracted with chloroform-methanol (2:1). The eluate was dried in vacuo to obtain 2′,4′-di-O-acetyl-23-O-(2-thienylacetyl)-23-demycinosyldesmycosin (100 mg, yield: 42.3%).

TLC: $Rf_a = 0.55$

The above product (89 mg) was dissolved in methanol (5 ml) and the solution was stirred at 55° C. for 5 hours. The methanol was distilled off in vacuo, and the residue dissolved in chloroform (20 ml) was washed with dil. aq. ammonia. The aqueous layer was extracted with chloroform (20 ml). The combined chloroform layer was dehydrated with anhydrous magnesium sulfate and dried in vacuo to obtain 23-O-(2-thienylacetyl)-23-demycinosyldesmycosin (65 mg, yield: 82%).

TLC: $Rf_b = 0.33$, $Rf_c = 0.38$

NMR (100 MHz, CDCl₃)δppm; 1.76 (s., 3H, C₁₂—CH₃), 2.50 (s., 6H, —N(CH₃)₂), 3.84 (s., 2H, thienyl—CH₂—), 4.15∼4.20 (m., 2H, 23—CH₂—), 4.26 (d., 1H, 1′-H), 4.95 (d.t., 1H, 15-H), 5.74 (d., 1H, 13-H, J=8.6 Hz), 6.28 (d., 1H, 10-H; J=15.7 Hz), 6.95 (m., 2H, thiophene ring 3.4-H), 7.24 (m., 1H, thiophene ring 5-H), 7.26 (d., 1H, 11-H), 9.71 (s., 1H, CHO)

EXAMPLE 3

23-O-phenylacetyl-23-demycinosyldesmycosin:

2',4'-di-O-acetyl-23-demycinosyldesmycosin (200 mg, 0.2934 mM), phenylacetic acid (39.9 mg, equimolar) and 4-dimethylamino pyridine (3.6 mg, 0.1 molar excess) was dissolved in dichloromethane (1 ml). A dichloromethane (1 ml) solution of DCC (60.4 mg, equimolar) was added at 0° C. thereto, and the mixture was stirred at room temperature for 23 hours. The insolubles were removed by filtration, and the filtrate was added to dil. aq. ammonia (5 ml), then extracted three times with chloroform (20 ml). The combined chloroform layer was dried with anhydrous magnesium sulfate, and concentrated in vacuo. The residue was purified by silica gel preparative TLC (developer: benzene-acetone, 3:1). The fractions showing $Rf_a=0.55$ were scratched off and extracted with chloroform-methanol (2:1). The extract was dried in vacuo to obtain 2',4'-di-O-acetyl-23-O-phenylacetyl-23-demycinosyldesmycosin (186 mg, yield: 79.2%).

TLC: $Rf_a=0.55$

The above product (166 mg) was dissolved in methanol (5 ml) and the solution was stirred at 55° C. for 5 hours. The methanol was removed in vacuo, and the residue dissolved in chloroform (20 ml) was washed with dil. aq. ammonia. The aqueous layer was extracted with chloform (20 ml). The combined chloroform layers were dehydrated with anhydrous magnesium sulfate and dried to obtain 23-O-phenyl-acetyl-23-demycinosyldesmycosin (122 mg, yield: 82%).

TLC; $Rf_b=0.33$, $Rf_c=0.36$

NMR (100 MHz, CDCl$_3$)δppm; 1.72 (s., 3H, C$_{12}$—CH$_3$), 2.50 (s., 6H, —N(CH$_3$)$_2$), 3.26 (s., 2H, phenyl —CH$_2$—), 4.15 (m., 2H, 23-CH$_2$), 4.26 (d., 1H, 1'-H), 4.90 (d.t., 1H, 15-H), 5.70 (d., 1H, 13-H, J=9.6 Hz), 6.26 (d., 1H, 10-H, J=1.57 Hz), 7.24 (d., 1H, 11-H), 7.28 (s., 5H, phenyl proton), 9.71 (s., 1H, CHO):MS(CI); 716 (MH+), 698 (MH+—H$_2$O), 598, 192, 174, 137

EXAMPLE 4

23-O-phenylthioacetyl-23-demycinosyldesmycosin:

In Example 3, phenylacetic acid (39.9 mg) was replaced by phenylthioacetic acid (49.3 mg) to obtain 2',4'-di-O-acetyl-23-O-phenylthioacetyl-23-demycinosyldesmycosin (84 mg, yield: 36.7%) ($Rf_a=0.55$).

The above product (76 mg) was subjected to de-diacetylation according to Example 2, to obtain 23-O-phenylthioacetyl-23-demycinosyldesmycosin (39 mg, yield: 55%).

TLC; $Rf_b=0.32$, $Rf_c=0.35$ NMR (100 MHz, CDCl$_3$)δppm; 1.76 (s., 3H, C$_{12}$—CH$_3$), 2.50 (s., 6H, —N(CH$_3$)$_2$), 3.65 (s., 2H, —CO—CH$_2$—S—), 4.0~4.4 (m., 3H, 23—CH$_2$—, 1'-H), 4.90 (t.d., 1H, 15-H), 5.65 (d., 1H, 13-H, J=10 Hz), 6.26 (d., 1H, 10-H, J=15.7 Hz), 7.23 (d., 1H, 11-H), 7.26 (d., 5H, phenyl proton), 9.71 (s., 1H, CHO)

EXAMPLE 5

23-O-cinnamoyl-23-demycinosyldesmycosin:

2',4'-di-O-acetyl-23-demycinosyldesmycosin (200 mg, 0.2934 mM), trans-cinnamic acid (43.4 mg, equimolar) and 4-dimethylamino pyridine (3.6 mg, 0.1 molar excess) were dissolved in dichloromethane (4 ml). A dichloromethane (1 ml) solution of DCC (60.4 mg, equimolar) was added thereto at 0° C. and the mixture was stirred at room temperature for 15 hours.

The reaction mixture was treated the same as in Example 2 to obtain 2',4'-di-O-acetyl-23-O-cinnamoyl-23-demycinosyldesmycosin (187 mg, yield: 78.5%) ($Rf_a=0.55$). The said product (182 mg) was de-diacetylated according to the method in Example 3 to obtain 23-O-cinnamoyl-23-demycinosyldesmycosin (140 mg, yield: 86%).

TLC; $Rf_b=0.39$, $Rf_c=0.38$

NMR (100 MHz, CDCl$_3$)δppm; 1.83 (s., 3H, C$_{12}$—CH$_3$), 2.51 (s., 6H, —N(CH$_3$)$_2$), 4.2~4.4 (m., 3H, 23—CH$_2$—, 1'-H), 5.02 (d.t., 1H, 15-H), 5.86 (d., 1H, 13-H), 6.30 (d., 1H, 10-H), 6.43 (d., 1H, 12-H), 7.12 (d., 1H, C═CH—), 7.42 (m., 5H, phenyl proton), 7.70 (d., 1H, phenyl —CH═), 9.70 (s., 1H, CHO) MS (CI); 728 (MH+), 710 (MH+—H$_2$O), 598, 537, 519, 192, 174, 149

EXAMPLE 6

23-O-[D(—)-α-amino-phenylacetyl]-23-demycinosyldesmycosin:

A dichloromethane (1 ml) solution of DCC (60.4 mg, equimolar) was added to 0° C. to 2',4'-di-O-acetyl-23-demycinosyldesmycosin (200 mg, 0.2934 mM), N-t-butoxycarbonyl-D-(—)phenylglycine (74 mg, equimolar) and 4-dimethylamino pyridine (3.6 mg, 0.1 molar excess) dissolved in dichloromethane (2 ml), and stirred for 90 minutes. The reaction mixture was treated as the same as in Example 3 to obtain 2',4'-di-O-acetyl-23-O-[D(—)-α-t-butoxy-carbonylaminophenylacetyl]-23-demycinosyldesmycosin (281 mg, yield: 95.2%).

The above product (276 mg) was de-diacetylated according to Example 3 to obtain 23-O-[D(—)-α-t-butoxycarbonylaminophenylacetyl]-23-demycinosyldesmycosin (210 mg, yield: 84%).

Trifluoroacetic acid (1 ml) was added to the above product (210 mg) and the mixture was stirred at room temperature for 30 minutes. The reaction mixture was adjusted to pH 8-9 with 7% aq. ammonia, and extracted with chloroform (100 ml). The chloroform layer was washed with water, dried with anhydrous magnesium sulfate, then concentrated in vacuo.

The residue was purified by silica gel preparative TLC (developer: chloroform-methanol=5:1).

The band showing $Rf_b=0.13$ and $Rf_c=0.34$ was collected and extracted with chloroform-methanol (2:1).

The extract was dried in vacuo to obtain 23-O-[D(—)-α-amino-phenyl-acetyl]-23-demycinosyldesmycosin (144 mg, yield: 78%).

TLC; $Rf_b=0.13$, $Rf_c=0.34$

NMR (100 MHz, CDCl$_3$)δppm; 1.84 (s., 3H, C$_{12}$—CH$_3$), 2.52 (s., 6H, N(CH$_3$)$_2$), 4.5~5.2 (m., 3H, 15-H, NH$_2$), 4.77 (s., 1H, CH-NH$_2$), 6.05 (d., 1H, 13-H, J=10 Hz), 6.31 (d., 1H, 10-H, J=15.4 Hz), 7.30 (m., 5H, phenyl proton), 7.68 (s., 1H, CHO), 7.82 (d., 1H, 11-H) MS (CI); MH+ not seen, 192, 174, 156, 137

EXAMPLE 7

23-O-(α-phenylbutyryl)-23-demycinosyldesmycosin:

2',4'-di-O-acetyl-23-demycinosyldesmycosin (200 mg, 0.2934 mM), α-phenylbutyric acid (48.2 mg, equimolar) and 4-dimethylamino pyridine (3.6 mg, 0.1 molar excess) were dissolved in dichloromethane (2 ml).

A dichloromethane (1 ml) solution of DCC (60.4 mg, equimolar) was added at 0° C. thereto and the mixture was stirred for 45 minutes. The reaction mixture was treated the same way as in Example 3 to obtain 2',4'-di-O-acetyl-23-O-(α-phenylbutyryl)-23-demycinosyldesmycosin (189 mg, yield: 77.8%).

This product was de-diacetylated by the same method as in Example 3 to obtain 23-O-(α-phenylbutyryl)-23-demycinosyldesmycosin (133 mg, yield: 78%).

TLC; Rf$_b$=0.29, Rf$_c$=0.41

NMR (100 MHz, CDCl$_3$)δppm: 1.65, 1.71 (each s., 3H, C$_{12}$—CH$_3$), 2.55 (s., 6H, —N(CH$_3$)$_2$), 4.12 (d., 2H, 23—CH$_2$—), 4.27 (d., 1H, 1'-H), 4.86 (m., 1H, 15-H), 5.58, 5.69 (each d., 1H, 13-H), 6.23, 6.25 (each d., 1H, 10-H, J=15.7 Hz), 7.15, 7.22 (each d., 1H, 11-H), 7.28 (s., 5H, phenyl proton), 9.70 (s., 1H, CHO) MS(CI); 744 (MH$^+$), 726 (MH$^+$-H$_2$O), 553, 535, 192, 174, 1

EXAMPLE 8

23-O-[2-(2-chloroacetamido-thiazol-4-yl)-2-methoxyiminoacetyl]-23-demycinosyldesmycosin:

2',4'-di-O-acetyl-23-demycinosyldesmycosin (500 mg), 2-(2-chloroacetamide-thiazole-4-yl)-2-methoxyiminoacetic acid (203.8 mg) and 4-dimethylamino pyridine (9 mg) were dissolved in dichloromethane (10 ml).

A dichloromethane (3 ml) solution of DCC (151 mg) was added dropwise thereto. Insoluble materials were removed by filtration, and the filtrate was added to dil. aq. ammonia (20 ml) then extracted three times with chloroform. The combined chloroform layer was passed through Whatman filter paper 1PS and dried in vacuo to obtain a white foamy substance (800 mg). This substance was dissolved in a small amount of chloroform and charged on a column (2×20 cm) of silica gel (20 g), then eluted with chloroform. The fractions showing Rf$_a$=0.46 in TLC were collected and dried in vacuo to obtain white foamy 2',4'-di-O-acetyl-23-O-[2-(chloroacetamidothiazol-4-yl)-2-methoxyiminoacetyl]-23-demycinosyldesmycosin (322 mg). This product, dissolved in methanol (5 ml), was stirred at 55° C. for 2.5 hours. The methanol was removed in vacuo to obtain a white foamy substance (286 mg), which was purified by silica gel TLC (developer: chloroform-methanol-conc. aq. ammonia=10:1:0.1). The band showing Rf$_d$=0.27 was scratched off and extracted with chloroform-methanol (3:1). The extract was dried in vacuo to obtain 23-O-[2-(2-chloroacetamido-thiazol-4-yl)-2-methoxyiminoacetyl]-23-demycinosyldesmycosin (167 mg). This substance (51 mg) was further purified by silica gel TLC (developer: chloroform-methanol=4:1). The band showing Rf$_d$=0.31 was collected, extracted with chloroform-methanol (3:1), and dried in vacuo to obtain a purified pale yellowish foamy substance (19 mg).

NMR (100 MHz, CDCl$_3$)δppm; 1.82 (s., 3H, C$_{12}$—CH$_3$), 2.61 (s., 6H, —N(CH$_3$)$_2$), 4.02 (s., 3H, OCH$_3$), 4.32 (s., 2H, —CH$_2$Cl), 4.6~5.0 (m., 3H, 1'-H, 23—CH$_2$—), 5.25 (t.d., 1H, 15-H), 5.97 (d., 1H, 13-H), 6.29 (d., 1H, 10-H), 7.30 (d., 1H, 11-H), 7.37 (s., 1H, thiazole ring 5-H), 9.68 (s., 1H, CHO)

EXAMPLE 9

23-O-[2-(2-aminothiazol-4-yl)-2-methoxyiminoacetyl]-23-demycinosyldesmycosin:

23-O-[2-(2-chloroacetamido-thiazol-4-yl)-2-methoxyiminoacetyl]-23-demycinosyldesmyconsin (116 mg, 0.1354 mM), thiourea (21 mg, 2 molar excess) and sodium acetate trihydrate (36.4 mg, 2 molar excess) were dissolved in ethanol (5 ml) and the mixture was stirred at room temperature for 26 hours. The reaction mixture was adjusted to pH 8-9 by adding dil. aq. ammonia, and extracted three times with chloroform. The combined chloroform layer was passed through Whatman filter paper 1PS (trade name), and dried in vacuo to obtain a white powder (87 mg), which was purified by silica gel TLC (developer: chloroform-methanol=3:1). The band showing Rf$_d$=0.47 was scratched off and extracted with chloroform-methanol (3:1). The extract was passed through Whatman filter paper 1PS and dried in vacuo to obtain 23-O-[2-(2-aminothiazol-4-yl)-2-methoxyiminoacetyl]-23-demycinosyldesmycosin (45 mg).

TLC; Rf$_d$=0.47

NMR (100 MHz, CDCl$_3$)δppm; 1.80 (s., 3H), 2.54 (s., 6H), 4.00 (s., 3H), 4.25 (d., 1H, 1'-H), 4.46 (d., 2H, 23—CH$_2$—), 5.07 (t.d., 1H), 5.47 (br.s., 2H, NH$_2$), 5.97 (d., 1H), 6.29 (d., 1H), 6.80 (s., 1H), 7.34 (d., 1H), 9.70 (s., 1H) MS (CI); MH$^+$ not seen, 192, 174, 126

EXAMPLE 10

23-O-(2-phenyl-2-methoxyiminoacetyl)-23-demycinosyldesmycosin:

2',4'-de-O-acetyl-23-dimycinosyldesmycosin (200 mg, 0.2934 mM), 2-phenyl-2-methoxyimino-acetic acid (52.5 mg, equimolar) and 4-dimethylaminopyridine (0.1 molar excess) were dissolved in dichloromethane (4 ml). A dichloromethane (1 ml) solution of DCC (60.4 mg, equimolar) was added thereto and the mixture was stirred at room temperature for 26 hours. The insoluble materials were removed by filtration, and the filtrate was added to dil. aq. ammonia (5 ml), then extracted three times with chloroform (20 ml). The combined chloroform layer was passed through Whatman filter paper 1PS and concentrated in vacuo. The residue was charged on a column (4×3 cm) of silica gel (20 g), and eluted with chloroform (200 ml) and chloroform-methanol (200:1) in this order. The fractions showing Rf$_a$=0.40 were collected and dried in vacuo to obtain 2',4'-di-O-acetyl-23-(2-phenyl-2-methoxyiminoacetyl)-23-demycinosyldesmycosin (240 mg). This substance, dissolved in methanol (5 ml) was stirred at 55° C. for 2 hours, and the methanol was distilled off. The residue was charged on a column (3.5×3 cm) of silica gel (20 g), and eluted with chloroform-methanol (100:1) (200 ml), chloroform-methanol (75:1) (150 ml), chloroform-methanol (50:1) (100 ml), and chloroform-methanol (20:1) (260 ml), in this order. The fractions showing Rf$_d$=0.48 were collected and concentrated in vacuo to obtain 23-O-(2-phenyl-2-methoxyiminoacetyl)-23-demycinosyldesmycosin (81 mg, yield: 36.4%).

NMR (100 MHz, CDCl$_3$)δppm; 1.80 (s., 3H, C$_{12}$—CH$_3$), 2.51 (s., 6H, —N(CH$_3$)$_2$), 4.02 (s., 3H, OCH$_3$), 4.25 (d., 1H, 1'-H), 4.46 (m., 2H, 23—CH$_2$—), 5.00 (t d., 1H, 15-H), 5.83 (d., 1H, 13-H), 6.29 (d., 1H, 10-H), 7.29 (d., 1H, 11-H), 7.3~7.0 (m., 5H, phenyl proton), 9.69 (s., 1H, CHO) MS (CI); 759 (MH$^+$), 741 (MH$^+$—H$_2$O), 192, 180, 174

EXAMPLE 11

23-O-[α-(4-chlorophenoxy)-isobutyryl]-23-demycinosyldesmycosin:

2',4'-di-O-acetyl-23-demycinosyldesmycosin (200 mg, 0.2934 mM), α-(4-chlorophenoxy)-isobutyric acid (63.0 mg) and 4-dimethylaminopyridine (3.6 mg) were dissolved in dichloromethane (2 ml). A dichloromethane (1 ml) solution of DCC (60.4 mg) was added thereto and the mixture was stirred at room temperature for one hour. The insoluble materials were filtered off, and the filtrate was added to dil. aq. ammonia (5 ml) and extracted three times with chloroform (20 ml). The combined chloroform layer was dehydrated with anhydrous magnesium sulfate and concentrated in vacuo. The residue was purified by silica gel TLC (20×20 cm, 2 plates, Merck, Art 5717) (developer: benzene-acetone=3:1). The band showing Rf$_a$=0.52 was scratched off and extracted with chloroform-methanol (3:1). The extract was dried in vacuo to obtain 2′,4′-di-O-acetyl-23-O-[α-4-(chlorophenoxy)isobutyryl]-23-demycinosyldesmycosin (199 mg).

TLC: $Rf_a$=0.52

This product, dissolved in methanol (5 ml), was stirred at 55° C. for 4.5 hours. The methanol was distilled off in vacuo and the residue was dissolved in chloroform (20 ml). The combined chloroform layer was dehydrated with anhydrous magnesium sulfate and dried in vacuo to obtain 23-O-[α-(4-chlorophenoxy)-isobutyryl]23-demycinosyldesmycosin (164 mg, yield: 70.3%).

TLC: $Rf_c$=0.23

NMR (100 MHz, CDCl$_3$)δppm; 1.58 (s., 6H,

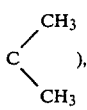

1.74 (s., 3H, $C_{12}$—CH$_3$), 2.50 (s., 6H, —N(CH$_3$)$_2$), 4.22 (d., 2H, 23—CH$_2$—), 4.25 (d., 1H, 1′-H), 4.85 (d.t., 1H, 15-H), 5.68 (d.), 6.27 (d.), 6.74 (d.t.,

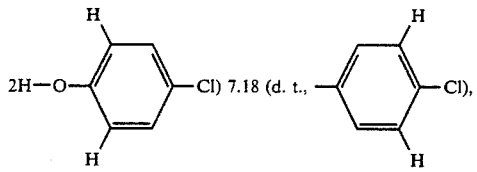

7.23 (d, 1H, $H_{13}$), 9.70 (s., 1H, CHO)

EXAMPLE 12

23-O-diphenylacetyl-23-demycinosyldesmycosin:

2′,4′-di-O-acetyl-23-demycinosyldesmycosin (200 mg, 0.2934 mM), diphenylacetic acid (62.2 mg) and 4-dimethylamino pyridine (3.6 mg, 0.1 molar excess) were dissolved in dichloromethane (1 ml). A dichloromethane (1 ml) solution of DCC (60.4 mg, equimolar) was added thereto at 0° C. and the mixture was stirred at room temperature for 0.5 hour. The insoluble materials were removed by filtration and the filtrate was added to dil. aq. ammonia (5 ml) and extracted three times with chloroform. The combined chloroform layer was dried with anhydrous magnesium sulfate and concentrated in vacuo. The residue (about 200 mg) was purified by silica gel TLC (developer: benzene-acetone=3:1). The band showing $Rf_a$=0.65 and $Rf_c$=0.92 was scratched off and extracted with chloroform-methanol (3:1). The eluate was dried in vacuo to obtain 2′,4′-di-O-acetyl-23-O-diphenylacetyl-23-demycinosyldesmycosin (170 mg).

TLC: $Rf_a$-0.65, $Rf_c$-0.92

This product dissolved in methanol (5 ml) and the solution was stirred at 55° C. for 3 hours. The methanol was distilled off in vacuo, and the residue, dissolved in chloroform (20 ml), was washed with dil. aq. ammonia. The aqueous layer was extracted with chloroform (20 ml). The combined chloroform layer was dehydrated with anhydrous magnesium sulfate and dried in vacuo to obtain 23-O-diphenylacetyl-23-demycinosyldesmycosin (149 mg, yield: 64.1%).

TLC: $Rf_c$=0.31

NMR (100 MHz, CDCl$_3$)δppm; 1.68 (s., 3H, $C_{12}$—CH$_3$), 2.51 (s., 6H, —N(CH$_3$)$_2$), 4.18~4.35 (m., 3H, 23—CH$_2$, 1′-H), 4.85 (d.t., 1H, 15-H), 5.02 (s., 1H, CH.Ph$_2$), 5.64 (d., 1H, 13-H), 6.24 (d., 1H, 10-H), 7.19 (d., 1H, 11-H), 7.28 (s., 10H, CPh$_2$), 9.71 (s., 1H, CHO) MS; 792 (MH$^+$), 774 (MH$^+$-18), 213, 192, 174

EXAMPLE 13

23-O-(2-phenylthio-2-phenylacetyl)-23-demycinosyldesmycosin:

In Example 12, diphenylacetic acid (62.2 mg) was replaced by 2-phenylthio-2-phenylacetic acid (71.6 mg) to obtain 2′,4′-di-O-acetyl-23-O-(2-phenylthio-2-phneylacetyl)-23-demycinosyldesmycosin (160 mg).

This product was de-diacetylated according to the method in Example 13 to obtain 23-O-(2-phenylthio-2-phneylacetyl)-23-demycinosyldesmycosin (142 mg, yield: 58.7%).

TLC: $Rf_c$=0.31

NMR (100 MHz, CDCl$_3$)δppm; 1.67 (s., 3H, $C_{12}$—CH$_3$), 2.51 (s., 6H, —N(CH$_3$)$_2$), 4.12 (m., 2H, 23—CH$_2$—), 4.26 (d., 1H, 1′-H), 4.84 (d.t., 1H, $H_{15}$), 4.91 (s., 1H,

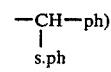

5.54 (br. d., 1H, 13-H), 6.24 (d., 1H, 10-H), 7.14, 7.18 (each d., 1H, 11-H), 7.29 (d., 10H, phenyl proton), 9.71 (s., 1H, CHO) MS; 824 (MH$^+$), 806 (MH$^+$—18), 245, 192, 174

EXAMPLE 14

23-O-(2-phenylsulfonyl-2-phenylacetyl)-23-demycinosyldesmycosin:

2′,4′-di-O-acetyl-23-demycinosyldesmycosin (200 mg, 0.2934 mM), 2-phenylsulfonyl-2-phenylacetic acid (810 mg) and 4-dimethylamino pyridine (3.6 mg, 0.1 molar excess) were dissolved in dichloromethane (2 ml). A dichloromethane solution (1 ml) of DCC (60.4 mg, equimolar) was added at 0° C. thereto, and the mixture was stirred at room temperature for 0.5 hour. The reaction mixture was treated by the same method as in Example 12 to obtain 2′,4′-di-O-acetyl-23-(2-phenylsulfonyl-2-phenylacetyl)-23-demycinosyldesmycosin (190 mg).

This product was de-diacetylated according to the method in Example 12 to obtain 23-O-(2-phenylsulfonyl-2-phneylacetyl)-23-demycinosyldesmycosin (159 mg, yield: 63.3%).

TLC: $Rf_c$=0.29

NMR (100 MHz, CDCl$_3$)δppm; 1.72, 1.73 (each s., 1H, $C_{12}$—CH$_3$), 2.50 (s., 6H, —N(CH$_3$)$_2$), 4.2~4.3 (m., 3H, 23—CH$_2$—, 1′-H), 4.84 (d.t., 1H, 15-H), 5.06, 5.07 (each s., 1H, CH-Ph), 5.63 (d., 1H, 13-H), 6.26 (d., 1H, 10-H), 7.21 (d., 1H, 11-H), 7.30 (m., 5H, phenyl proton), 7.4~7.7 (m., 5H, SO$_2$-Ph), 9.70 (s., 1H, CHO) MS; MH$^+$ 233, 192, 174

EXAMPLE 15

2′-O-acetyl-23-demycinosyl-4′-deoxydesmycosin:

23-demycinosyl-4′-deoxydesmycosin (3.35 g) was dissolved in dichloromethane (20 ml). Acetic anhydride (1.36 ml, 2.5 molar excess) was added thereto with ice cooling, and the mixture was stirred at room temperature for 2.5 hours. The reaction mixture was poured into dil. aq. ammonia, and extracted with chloroform after checking the pH of the aqueous layer to be pH 8-9. The chloroform layer was washed with water, passed through Whatman filter paper 1PS, and concentrated in vacuo to obtain white foamy 2'-O-acetyl-23-demycinosyl-4'-deoxydesmycosin (3.56 g, yield: 99.1%).

TLC: $Rf_d=0.44$

NMR (100 MHz, CDCl$_3$)δppm; 1.82 (s.), 2.08 (s., 3H, OCOCH$_3$), 2.25 (s.), 3.74 (d.,), 4.24 (d.), 4.75 (d.d., 1H, 2'-H), 4.96 (d.t.), 5.88 (d.), 6.32 (d.), 7.34 (d.), 9.69 (s.) Mass (CI); 624 (MH+), 606 (MH+-18), 582 (MH+-42), 218, 200.

EXAMPLE 16

23-O-(2-thienylacetyl)-23-demycinosyl-4'-deoxydesmycosin:

2'-O-acetyl-23-demycinosyl-4'-deoxydesmycosin (200 mg), 2-thienylacetic acid (45.5 mg, equimolar) and 4-dimethylaminopyridine (3.9 mg, 0.1 molar excess) were dissolved in dichloromethane (2 ml). A dichloromethane (1 ml) solution of DCC (66.2 mg, equimolar) was added at 0° C. thereto, and the mixture was stirred at room temperature for one hour. The insoluble materials were removed by filtration and the filtrate was adjusted to pH 8–9 by adding dil. aq. ammonia, then extracted three times with chloroform (20 ml). The combined chloroform layer was passed through Whatman filter paper 1PS and concentrated in vacuo. The residue was purified by silica gel TLC (20×20 cm, 2 plates, Merck, Art 5717) (developer: chloroform-methanol-conc. aq. ammonia=100:10:1). The band showing Rf=0.68 was scratched off and extracted with chloroform-methanol (3:1). The extract was concentrated in vacuo to obtain 2'-O-acetyl-23-O-(2-thienylacetyl)-23-demycinosyl-4'-deoxydesmycosin (124 mg). This product was dissolved in methanol (5 ml), heated at 55° C. for 5 hours and concentrated in vacuo. The residue was adjusted to pH 8–9 by adding aq. ammonia and extracted with chloroform. The chloroform layer was passed through Whatman filter paper 1PS and concentrated in vacuo to obtain 23-O-(2-thienylacetyl)-23-demycinosyl-4'-deoxydesmycosin as a white foamy substance (82.0 mg, yield: 36.2%).

TLC: $Rf_c=0.52$

NMR (Fx-100, CDCl$_3$)δppm; 1.75 (s., 3H, C$_{12}$—CH$_3$), 2.26 (s., 6H, —N(CH$_3$)$_2$), 3.84 (s., 2H. —COCH$_2$), 4.20 (d, 3H. 1'-H and 23—CH$_2$, 4.93 (d.t., 1H, 15-H), 5.75 (d., 1H, 13-H), 6.30 (d., 1H, 10-H), 6.94 (m., 2H, thiophene ring 3, 4-H), 7.21 (m., 1H, thiophene ring 5-H), 7.29 (d., 1H, 11-H), 9.72 (s., 1H, CHO) Mass (CI); 706 (MH+), 688 (MH+-18), 176, 158, 143

EXAMPLE 17

23-O-phenylacetyl-23-demycinosyl-4'-deoxydesmycosin:

In Example 17, 2-thienylacetic acid (45.5 mg) was replaced by phenylacetic acid (43.6 mg) to obtain 2'-O-acetyl-23-phenylacetyl-23-demycinosyl-4'-deoxydesmycosin (110 mg) (Rf$_c$=0.71).

This product was de-acetylated according to Example 16 to obtain 23-O-phenylacetyl-23-demycinosyl-4'-deoxydesmycosin as a white foamy substance (75 mg, yield: 33.4%).

TLC: $Rf_c=0.53$

NMR (FX-100, CDCl$_3$)δppm: 1.72(s.), 2.26(s.), 3.62(s.), 4.17(m., 3H), 4.90(d.t.), 5.72 (d.), 6.29(d.), 7.26(d.), 7.28 (s., 5H, phenyl proton), 9.73(s.)

Mass(CI): 700(MH+), 682(MH+-18), 176, 158, 137.

EXAMPLE 18

23-O-phenylthioacetyl-23-demycinosyl-4'-deoxydesmycosin:

In Example 17, 2-thienylacetic acid (45.5 mg) was replaced by phenylthioacetic acid (53.9 mg) to obtain 2'-O-acetyl-23-phenylthioacetyl-23-demycinosyl-4'-deoxydesmycosin (133 mg) showing Rf$_c$=0.73. This compound was deacetylated according to Example 17 to obtain 23-O-phenylthioacetyl-23-demycinosyl-4'-deoxydesmycosin as a white foamy substance (81 mg, yield: 34.5%).

TLC: $Rf_c=0.55$

NMR (FX-100, CDCl$_3$)δppm; 1.74 (s.), 2.26 (s.), 3.65 (s.), 4.19 (m., 3H), 4.87 (d.t.), 5.66 (d.) 6.29 (d.), 7.25 (d.), 7.31 (m., 5H, phenyl proton), 9.72 (s.)

Mass (CI); 732 (MH+), 714 (MH+-18), 176, 169, 158

EXAMPLE 19

23-O-cinnamoyl-23-demycinosyl-4'-deoxydesmycosin:

In Example 17, 2-thienylacetic acid (45.5 mg) was replaced by trans-cinnamic acid (47.4 mg) to obtain 2'-O-acetyl-23-O-cinnamoyl-23-demycinosyl-4'-deoxydesmycosin (200 mg). This compound was dissolved in methanol (5 ml), heated at 55° C. for 3 hours, and concentrated in vacuo. The residue was adjusted to pH 8–9 by adding dil. aq. ammonia and extracted with chloroform. The chloroform layer was passed through Whatman 1PS and concentrated in vacuo to obtain 23-O-cinnamoyl-23-demycinosyl-4'-deoxydesmycosin as a white foamy substance (139 mg, yield: 60.8%).

TLC: $Rf_c=0.54$

NMR (FX-100, CDCl$_3$)δppm; 1.82 (s.), 2.26 (s.), 4.17~4.32 (m., 3H), 5.00 (d.t.), 5.89 (d.), 6.32 (d.), 6.43 (d) 7.34 (d), 7.42 (m., 5H, phenyl proton), 7.70 (d., 1H, CH-Ph), 9.72 (s.)

Mass (CI); 712 (MH+), 694 (MH+-18), 176, 158, 149

EXAMPLE 20

23-O-(α-phenylbutyryl)-23-demycinosyl-4'-deoxydesmycosin:

In Example 16, 2-thienylacetic acid (45.5 mg) was replaced by α-phenylbutyric acid (52.6 mg) to obtain 2'-O-acetyl-23-(α-phenylbutyryl)-23-demycinsoyl-4'-deoxydesmycosin (200 mg) (Rf$_c$=0.76). This substance was deacetylated according to Example 20 to obtain 23-O-(α-phenylbutyryl)-23-demycinosyl-4'-deoxydesmycosin as a white foamy substance (159 mg, yield: 68.1%).

TLC: $Rf_c=0.49$

NMR (FX-100, CDCl$_3$)δppm; 1.65, 1.70 (each s., 2.27 (s.), 4.10~4.28 (m., 3H), 4.84 (d.t.), 5.66, 5.72 (each d.), 6.26, 6.28 (each d.), 7.20, 7.25 (each d.), 7.28 (s., 5H, phenyl proton), 9.73 (s.)

Mass (CI); 7.28 (MH+), 7.10 (MH+-18), 176, 158

What is claimed is:

1. A compound of the formula

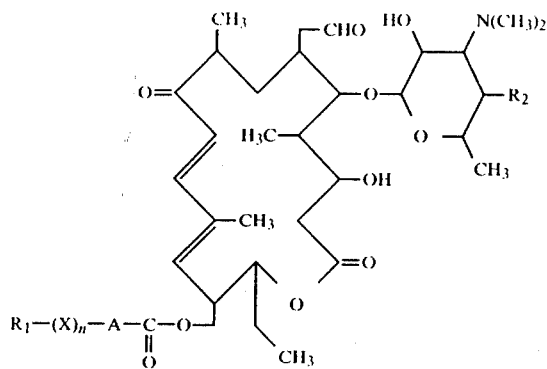

wherein R₁ is optionally substituted phenyl, thienyl, 2-amino-4-thiazolyl or 2-chloroacetamido-4-thiazolyl; A is lower alkylene, lower alkenylene, or lower alkylene substituted by lower alkyl, amino, lower alkoxyimino or phenyl-Z-group wherein Z is a single bond or —S— or —SO₂—, but when R₁ is 2-amino-4-thiazolyl or 2-chloroacetamido-4-thiazolyl then A is lower alkylene substituted by lower alkoxyimino; R₂ is hydrogen or hydroxyl; X is oxygen or sulfur and n=0 or 1, or a non-toxic salt thereof.

2. A compound according to claim 1 wherein the said compound is a compound selected from the group consisting of the following:

23-O-phenylacetyl-23-demycinosyldesmycosin,
23-O-phenylthioacetyl-23-demycinosyldesmycosin,
23-O-(α-phenylbutyryl)-23-demycinosyldesmycosin,
23-O-[D(—)-α-amino-phenylacetyl]-23-demycinosyldesmycosin,
23-O-cinnamoyl-23-demycinosyldesmycosin,
23-O-(2-phenyl-2-methoxyiminoacetyl)-23-demycinosyldesmycosin,
23-O-(2-thienylacetyl)-23-demycinosyldesmycosin,
23-O-[2-(2-chloroacetamido-thiazol-4-yl)-2-methoxyiminoacetyl]-23-demycinosyldesmycosin,
23-O-[2-(2-aminothiazol-4-yl)-2-methoxyiminoacetyl]-23-demycinosyldesmycosin,
23-O-[α-(4-chlorophenoxy)isobutyryl]-23-demycinosyldesmycosin,
23-O-diphenylacetyl-23-demycinosyldesmycosin,
23-O-(2-phenylthio-2-phenylacetyl)-23-demycinosyldesmycosin,
23-O-(2-phenylsulfonyl-2-phenylacetyl)-23-demycinosyldesmycosin,
23-O-phenylacetyl-23-demycinosyl-4'-deoxydesmycosin,
23-O-phenylthioacetyl-23-demycinosyl-4'-deoxydesmycosin,
23-O-(α-phenylbutyryl)-23-demycinosyl-4'-deoxydesmycosin,
23-O-cinnamoyl-23-demycinosyl-4'-deoxydesmycosin,
23-O-(2-phenyl-2-methoxyiminoacetyl)-23-demycinosyl-4'-deoxydesmycosin,
23-O-[D(—)-α-amino-phenylacetyl]-23-demycinosyl-4'-deoxydesmycosin,
23-O-(2-thienylacetyl)-23-demycinosyl-4'-deoxydesmycosin,
23-O-[2-(2-chloroacetamido-thiazol-4-yl)-2-methoxyiminoacetyl]-23-demycinosyl-4'-deoxydesmycosin, and
23-O-[2-(2-aminothiazol-4-yl)-2-methoxyiminoacetyl]-23-demycinosyl-4'-deoxydesmycosin.

* * * * *

UNITED STATES PATENT AND TRADEMARK OFFICE
CERTIFICATE OF CORRECTION

PATENT NO. : 4,490,524
DATED : December 25, 1984
INVENTOR(S) : Tatsuro FUJIWARA et al.

It is certified that error appears in the above—identified patent and that said Letters Patent is hereby corrected as shown below:

Column 17, lines 25 and 26, cancel "or hydroxyl";

Column 17, cancel lines 31-36;

Column 18, cancel lines 1-15.

Signed and Sealed this

Thirtieth Day of April 1985

[SEAL]

Attest:

DONALD J. QUIGG

Attesting Officer  Acting Commissioner of Patents and Trademarks